(12) United States Patent
Chon (10) Patent No.: US 6,418,780 B1
(45) Date of Patent: Jul. 16, 2002

(54) CERAMIC GAS SENSOR AND AN APPARATUS FOR MEASURING WASTE GAS USING THE SENSOR AND CONTROLLING AN AMOUNT OF FUEL TO BURN

(75) Inventor: Young Kap Chon, Kyungsangnam-do (KR)

(73) Assignee: Korea Electrotechnolgy Research Institute, Kyungsangnam-do (KR)

( * ) Notice: Subject to any disclaimer, the term of this patent is extended or adjusted under 35 U.S.C. 154(b) by 0 days.

(21) Appl. No.: 09/706,730

(22) Filed: Nov. 7, 2000

(30) Foreign Application Priority Data

Nov. 8, 1999 (KR) ............................................. 99-49276

(51) Int. Cl.⁷ ........................ G01N 33/497; G01N 27/26
(52) U.S. Cl. ...................................... 73/23.32; 204/425
(58) Field of Search ............................ 73/31.05, 23.32; 204/424, 425

(56) References Cited

U.S. PATENT DOCUMENTS 5,124,021 A * 6/1992 Kaneyasu et al. .......... 204/425
5,360,528 A * 11/1994 Oh et al. .................... 204/425
5,413,691 A * 5/1995 Kaneyasu et al. .......... 204/424
5,505,837 A * 4/1996 Friese et al. ................ 204/425

\* cited by examiner

*Primary Examiner*—Hezron Williams
(74) *Attorney, Agent, or Firm*—Arent Fox Kintner Plotkin & Kahn PLLC

(57) ABSTRACT

The present invention relates to an apparatus for measuring and displaying a noxious waste gas exhausted from a vehicle in real time through an electrical method instead of conventional chemical one, and controlling an amount of fuel to feed an engine with based on the measurement result to adjust an amount of noxious gas generated. A sensor, which is an element of the present invention, comprises a porous ceramic and a pair of electrodes to apply a voltage across two sides of the porous ceramic. A whole system for controlling an amount of fuel to burn, comprises the sensor, which is installed onto an exhaust pipe, generating a leakage current proportional to an amount of conductive particles contained in a waste gas; a measuring unit computing an amount of gas composition based on the generated leakage current; a controlling unit adjusting an amount of fuel to be fed into the engine from a fuel tank based on the computed value for the amount of gas composition; and a displaying unit displaying the computed values numerically or turning on a LED to alarm under the control of the controlling unit if one of the computed values exceeds a preset limit.

3 Claims, 5 Drawing Sheets

FIG. 1

Conventional Art

CERAMIC GAS SENSOR AND AN APPARATUS FOR MEASURING WASTE GAS USING THE SENSOR AND CONTROLLING AN AMOUNT OF FUEL TO BURN

BACKGROUND OF THE INVENTION

1. Field of the Invention

This invention relates to an apparatus for measuring and displaying an amount of a noxious waste gas exhausted from a vehicle in real time, and controlling an amount of fuel to be fed into an engine based on the measurement result.

2. Description of the Related Art

According to the waste gas regulation, an automobile should take a waste gas test at regular intervals and when it acquires a formal approval after manufactured. In a test room, an automobile should be driven under a specified condition in a test room in order to measure accurately noxious substances contained in a waste gas that would be exhausted while the automobile is being driven on a road.

And, various complicated devices are connected with a test equipment. For example, a chassis dynamometer simulates the air resistance, the road slope, the driving resistance, and so on, to apply various practical driving conditions of many roads to a car being tested. While a car is being driven with a chassis dynamometer, an engine is cooled by a cooling fan positioned at the front of a car, and a waste gas exhausted during the test driving is caught. After the test driving done, the caught waste gas is analyzed to measure noxious substances contained in a waste gas.

A test method and regulated volume about a waste gas are mostly different between all countries. The level of testing technology is also differentiated as well. However, a testing procedure for measuring an amount of noxious gases has been agreed internationally. The CVSD (Constant Volume Sampling Dilution) method has been adopted and generalized as a standard testing procedure since 1982, however, the CVSD method is conducted a little differently according to each country.

Figure 1:
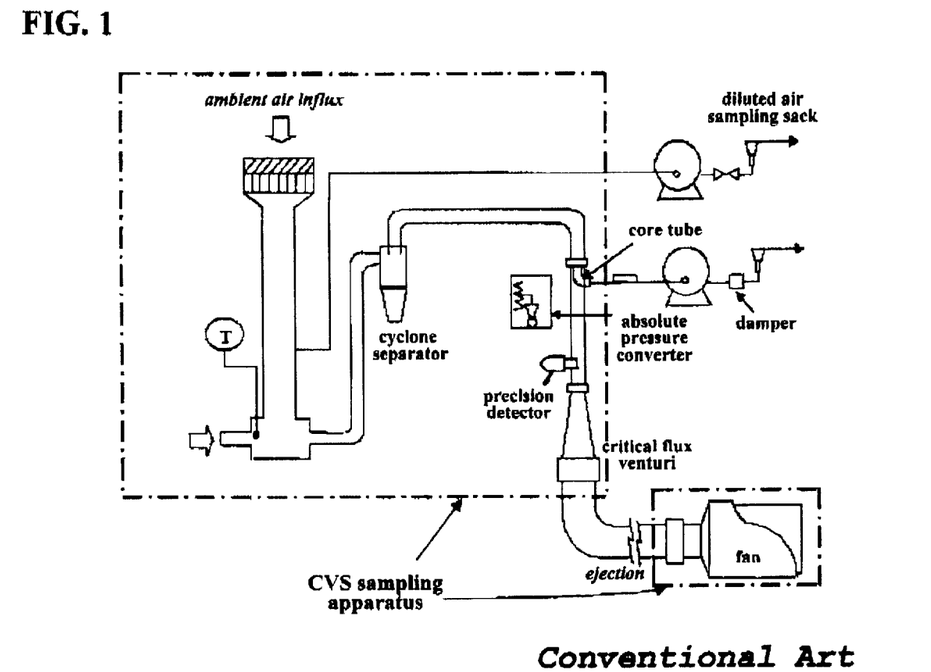
FIG. 1 shows a schematic process diagram for conducting the conventional CVSD method.

FIG. 1 shows a schematic process diagram for conducting the CVSD method. In the CVSD method, if a car exhausts a waste gas while being driven according to a test driving cycle sequence, the waste gas is diluted through being mingled with the air after filtered, and then is inhaled by a special pump. The diluting air volume is adjusted in the total volume flow of an exhaust gas and diluting air to maintain the ratio of the diluting air to total volume flow to be constant.

However, in the CVSD method, a measuring apparatus should be highly precise enough to detect minute change of the dilution ratio since the concentration of each noxious gas becomes low according to the dilution ratio. Moreover, the CVSD method can not be applied to a car being driven on the real road.

The conventional waste gas measuring method including the aforementioned CVSD method is on the basis of chemical analysis. This chemical-based measuring method is very sensitive to ambient temperature, humidity, and so on, so that a chemical-based measuring apparatus developed to be insensitive to the atmospheric factors is very expensive and its operating method is also very complicated. Therefore, the conventional measuring apparatus adopting chemical analyzing method can not be distributed over every measuring post on the road, and it is not applicable to measure noxious gases exhausted from a moving car in real time either.

SUMMARY OF THE INVENTION

It is an object of the present invention to provide a ceramic gas sensor being able to sense a noxious waste gas electrically in real time.

It is another object of the present invention to provide an apparatus for displaying an amount of a noxious waste gas being exhausted and controlling an amount of fuel to feed an engine with based on a measured data for a noxious waste gas.

A waste gas sensor according to the present invention comprises a porous ceramic in which pores are formed; an insulating supporter supporting the porous ceramic at the bottom of the porous ceramic; an insulating filler covering the porous ceramic; a pair of electrodes inserted vertically into the porous ceramic through the insulating filler and separating them into three parts; a pair of thermal compensating plates, which are inserted vertically into the insulating filler to support the pair of electrodes, transforming an electrical energy into a thermal energy; lead wires connected to each of the electrodes and the thermal compensating plates; and an insulating lid covering the top of the filler and separating the lead wires each other, wherein the lead wires penetrate the lid.

A fuel controlling apparatus according to the present invention comprises the waste gas sensor, which is installed in an exhaust pipe, generating a leakage current proportional to an amount of conductive particles contained in a waste gas and maintaining its temperature constantly by transforming an electrical energy into a thermal energy; a measuring unit computing an amount of gas composition based on the generated leakage current; a controlling unit adjusting an amount of fuel to be fed into an engine from a fuel tank based on the computed value for the amount of gas composition; and a displaying unit displaying the computed values numerically or turning on a LED to alarm under the control of the controlling unit.

BRIEF DESCRIPTION OF THE DRAWINGS

The accompanying drawings, which are included to provide a further understanding of the invention, illustrate the preferred embodiments of the invention, and together with the description, serve to explain the principles of the present invention.

In the drawings.

DETAILED DESCRIPTION OF THE PREFERRED EMBODIMENT

In order that the invention may be fully understood, preferred embodiments thereof will now be described with reference to the accompanying drawings.

When a gas stream has permeated into open pore cells whose size is uniform, if an electric filed is applied across all of the open pore cells, the gas stream is partly ionized and arranged in a chain, so that a current flows through the arranged ion chain. In addition, even though the magnitude of the applied electric filed is same, the flowing current is different in magnitude according to which compositions the gas stream has.

A waste gas sensor according to the present invention uses this principle.

To use this principle, an electric circuitry includes an pore-formed absorbing unit having many pore cells. Conductive particles contained in a noxious waste gas adhere to the surface of each pore cell.

The electric circuitry would be a resistive circuit in which a resistor is inserted in a closed loop, and the magnitude of the resistor is determined by an amount of the adhered conductive particles. Therefore, since the equation of I=V/R is satisfied in the circuitry, if the applied voltage V is maintained constant, the induced leakage current changes in inverse proportional to the change of the resistance R, that is, the current changes according to the compositions of a noxious waste gas.

In other words, after a constant voltage is applied, it is possible to measure in real time an amount of conductive particles contained in hydrocarbons and other noxious gases by detecting leakage current variation. Therefore, it is possible to measure in real time an amount of noxious gases being exhausted from an automobile being driven on the road through measuring the leakage current, which means that it is possible to obtain data indicative of concentration of noxious gas in real time and to use the obtained data immediately in controlling fuel to be fed into an engine.

The above-explained sprit or essential characteristics of the present invention is explained now in detail.

In an embodiment of the present invention, hydrocarbon material is chosen as a measuring object to indicate how much a waste gas is harmful. The reason of this choice is as follows.

The crude oil, which is source of all kind of fuel, is a liquefied hydrocarbon mixture including a small portion of oxygen compound, nitrogen compound, sulfur compound, etc. The ratio of weight composition of crude oil is as follows. Carbon is 83~87%, hydrogen 11~14%, sulfur below 5%, oxygen below 0.5%, nitrogen below 0.4%, and the rest metallic components below 0.5%.

Referring to the composition ratio of a crude oil, we are able to know that a crude oil is mostly composed of carbon and hydrogen, therefore, hydrocarbon can be used as the index material to indicate how much a waste gas pollutes the atmosphere.

Eqs. (1) and (2) are hydrocarbon producing mechanism from paraffin series such as ethane and naphthalene series such as cyclo-propine, respectively.

$$C_2H_6 \rightarrow CH_4 + C + H_2 \quad (1)$$

$$C_3H_6 \rightarrow C_2H_4 + C + H_2 \quad (2)$$

In Eqs. (1) and (2), the free carbon C is conductive material which has such electrical characteristics that the radius of a charged particle is 0.16 Å, the resistance ratio 0.0019 Ω-cm, and the current density 9.5 A/cm². Using the electrical characteristics of a free carbon, an electrical circuit for a sensor can be designed.

The sensor for measuring the quantity of conductive particles through detecting a leakage current according to the present invention is made from ceramic, and has many pores to adhere conductive particles to their internal surfaces.

The porous ceramic sensor (PCS) should have thermal resistance to stand against heat above 1000° C. and strong impact resistance.

The PCS may be made from various inorganic compound, however, it is preferable to make the PCS out of alumina material of corundum structure which has face-centered cubic lattice. This structure has excellent chemical resistance.

The manufacturing method of the PCS is as follows. A ceramic powder is made to a slurry of colloid state which is then infiltrated into and coated on polyurethane foam with constant thick. After infiltration and coating, excessive slurry is removed, and then the coated slurry is dried. After these manufacturing processes done, the conventional ceramic manufacturing process is conducted.

If such-manufactured PCS is installed in an exhaust pipe of an automobile, then, through a portable measuring instrument or a remote controllable measuring instrument, it is possible to monitor in real time how much a waste gas exhausted from an automobile is harmful, and to control an amount of fuel to feed combustion chamber with based on the monitored value.

Since the PCS is made from ceramic which is an insulating material, it can be supposed that current density flowing along the direction of an electric field is very low at an initial condition with an electric field applied.

Figure 2:
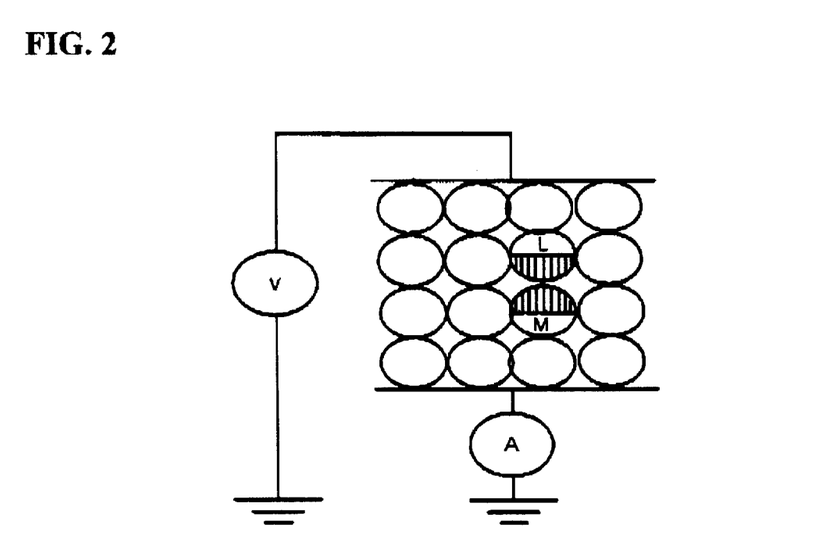
FIG. 2 shows an electrical model circuit of the adsorptive layer to calculate the conductivity generated at the adsorptive layer.
Figure 3:
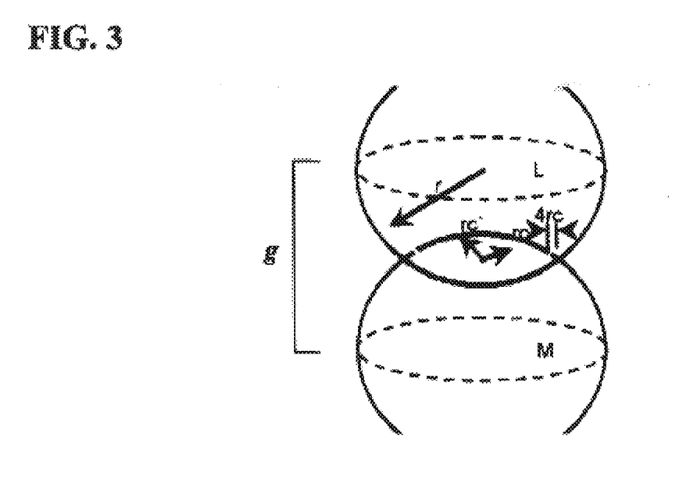
FIG. 3 shows a sectional condition having the conductivity between two neighboring layers.

Therefore, an ideal equation for change of quantity of electricity can be derived from the microscopic model circuit depicted in FIGS. 2 and 3.

FIG. 2 shows an electrical model circuit of the adsorptive layer to calculate the conductivity generated at the adsorptive layer, and FIG. 3 shows a sectional condition having the conductivity 'g' between two neighboring layers having parallel sections L and M.

The conductivity $\sigma_\lambda$ relating to sectional layers L and M is an element of conductivity 'g' which is constituted by serial-connected and parallel-connected $\sigma_1$, and it is given by the Eq. (3) since the connection is made 1/2r in series and 1/(2r)² in parallel.

$$\sigma_1 = g \cdot \frac{1/(2r)^2}{1/(2r)} = \frac{g}{2r} \quad (3)$$

where the conductivity 'g' is attained by parallel connection of ion particle leakage $R_f$ and ion particle self resistance $R_c$ between L and M.

The ion particle self resistance $R_c$ can be represented by the sum of contact point resistance $R_a$ existing at the contact point and the oxide film resistance $R_b$ at the contact surface.

The contact resistance $R_s$ is given by Eq. (4).

$$R_s = \frac{1}{2R_c'} \cdot \frac{1}{\delta_s} \ (\Omega) \quad (4)$$

where $\delta_s$ is particle self conductivity, $r_c'$ is the effective radius $r_c + \Delta r_c$ of the contact surface.

And, the oxide film resistance existing in the contact surface, that is, the resistance of the adsorptive molecular layer, is given by Eq. (5), $$R_s = \frac{\rho_b}{\pi \cdot r_c'^2} \quad (\Omega) \qquad (5)$$

where $\rho_b$ is conductivity of unit square area of the contact surface.

Accordingly, the ion particle self resistance $R_c$ is given by Eq. (6).

$$R_c = \frac{1}{2r_c' \cdot \delta_s} + \frac{\rho_h}{\pi \cdot r_c'^2} \quad (\Omega) \qquad (6)$$

In case that the capillary condensation of water molecular is neglected, $r_c'$ becomes $r_c$ on the contacting point at low temperature, however it is increased by $\Delta r_c$ at high temperature since the capillary condensation of water molecular can not be neglected.

Next, considering the conductivity of the particle surface, the surface leakage $R_f$ is given by Eq. (7).

$$R_f = \frac{\ln(2r/r_c')}{\pi \cdot \sigma_f} \quad (\Omega) \qquad (7)$$

Therefore, the conductivity $\sigma_1$ of the ideal adsorptive layer of FIG. 3 is given by Eq. (8), and it is understood that the constituting parameters are $r_c$, $r_c'$, $\delta_a$, $\delta_f$ and $\rho_b$.

$$\sigma_1 = \frac{r_c'/r}{1 + (2\delta_s \cdot \rho_h/\pi r_c')} \cdot \delta_s + \frac{\pi/2r}{\ln(2r/r_c')} \cdot \delta_f \qquad (8)$$

From Eq. (8), it is clear that it is possible to measure an exhaust gas by detecting the magnitude of leakage current indicative of the quantity of ionized particles contained in the conductive gas of a waste gas when a conductive gas stream passes through the sensor while being absorbed to pores formed in the sensor.

In the derivation of Eq. (8), it is assumed that the pores formed in the sensor is ball-shaped, however, even though the internal shape of the pore is irregular, Eq. (8) is applicable if it is compensated by a shape factor. And, it is also applicable even when a conductive path is made due to passage of hydrocarbon (HC) contained in a waste gas.

In the condition that the charge density and mobility is low in the sensor material, the electrical model circuit of the adsorptive layer shown in FIG. 2 can be used for thermal and chemical factors as well as electrical factor.

Figure 4:
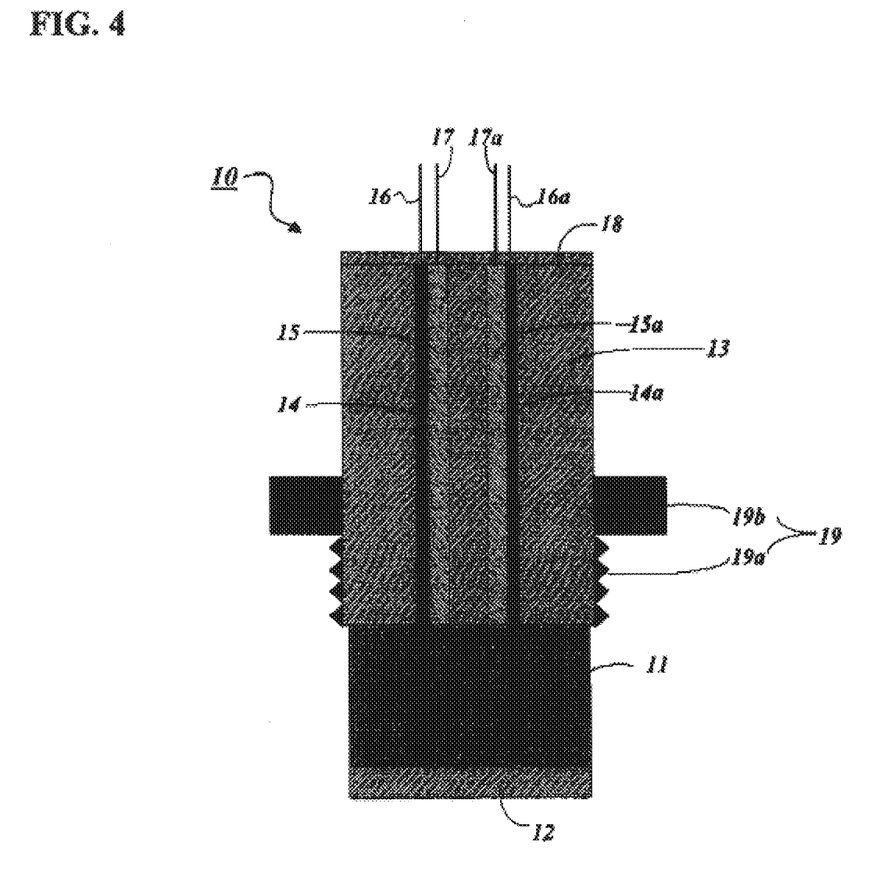
FIG. 4 is longitudinal-sectional-viewed structure of a waste gas sensor according to the present invention.

FIG. 4 is schematic structure of a waste gas sensor according to the present invention.

The sensor 10 of FIG. 4 comprises cylindrical porous ceramic 11 in which constant-sized pores are formed; a disk-shaped insulating plate 12 supporting the cylindrical ceramic 11; a cylindrical insulating filler 13 formed on the cylindrical ceramic 11; two rectangular electrodes 14 and 14a inserted downward into the cylindrical ceramic 11 through the filler 13 as dividing them into three parts; two thermal compensating rectangular plates 15 and 15a inserted downward into the filler 13 to transform electrical energy to thermal and to support the electrodes 14 and 14a by the side of them; lead wires 16, 16a, 17, and 17a connected to the electrodes 14 and 14a and the thermal compensating plates 15 and 15a, respectively; an insulating lid 18 covering the top of the filler 13 and separating the lead wires 16, 16a, 17, and 17a each other, which penetrate the lid 18; a combining unit 19 consisting of a male screw 19a and a screw cap 19b formed around the peripheral of the filler 13.

The electrodes 14 and 14a are made from stainless steel or stainless steel etched by plating 1 mm×1 mm as the size of the mesh. In processing of the mesh, the surface should be very smooth by etching with an electron beam. The combining unit 19 should be made from material of strong heat resistance. In addition, the electrodes 14 and 14a are separated by voltage withstanding distance and are fixed by the insulating filler 13, and the lead wires 16, 16a, 17, and 17a are also separated each other by voltage withstanding distance and are fixed by the insulating lid 18.

The thermal compensating plates 15 and 15a support the electrodes 14 and 14a as well as generate heat energy to raise initial temperature. The thermal compensating plates 15 and 15a transform electrical energy provided through the lead wires 17 and 17a into thermal energy which heats up an exhaust pipe to keep constant warm temperature when an exhaust pipe is cold at start up. Due to this temperature compensation, an ionized gas is so activated that an optimal condition to obtain accurate data is set up.

When the sensor 10 embodying the present invention is to be installed onto an exhaust pipe, the exhaust pipe is drilled at first, and a female screw corresponding to the male screw 19a is formed around inner peripheral of the drilled hole. Then, the sensor 10 is tightly combined with the exhaust pipe through screw combination. The screw cap 19b is used to adjust the insertion depth into the hole and to seal the gap between the sensor 10 and the exhaust pipe to prevent a waste gas from being effused through the gap.

TABLE 1

| Material | Porous Ceramic |
|---|---|
| Size of Pore | above 300 μm |
| External diameter of the sensor | 5–20 mm |
| Height of the sensor | 50 mm |
| Constituent | 98% $Al_2O_3$ |
| Coefficient of thermal expansion | (6.5~8.5) × $10^{-6}$/° C. |
| Specific gravity | 0.75–0.85 |
| Pore ratio | 75–85% |

The characteristics of the cylindrical porous ceramic 11 and the specification of the sensor 10 shown in FIG. 4 are given by table 1.

The pore ratio is obtained by Eq. (9).

$$\text{Pore} \cdot \text{Ratio} = \frac{V_3}{V_1 + V_2 + V_3} \times 100(\%) \qquad (9)$$

where $V_1$ is volume of ceramic material, $V_2$ is volume of pore part, and $V_3$ is volume of open pore.

The filler 13 and the insulating plate 12 are made from basic material of 96% alumina, and their characteristics are given by table2.

TABLE 2

| Physical properties | Alumina content | 96% |
|---|---|---|
| | Absorption rate | Below 0.1% |
| | Specific gravity | 3.1–3.4 |
| Mechanical characteristics | hardness | 9.0 Moh's |
| | Compressive strength | 22500 Kg/cm$^2$ |
| | Bending strength | 2600–3500 Kg/cm$^2$ |
| Thermal characteristics | Safe temperature in continuous use | 1600° C. |
| | Thermal expansion coefficient | 7.2 × $10^{-6}$/° C. |

TABLE 2-continued

| | | |
|---|---|---|
| | Thermal conductivity(250C) | 0.05 Cal/cm.sec.° C. |
| Electrical characteristics | Volume resistance | >1014 Ω.Cm |
| | Dielectric Strength | 14 KV/mm |
| | Dielectric constant | 9.6 MHz 25° C. |
| | Dielectric power factor | 0.0003 MHz (tanδ) |

Figure 5A:
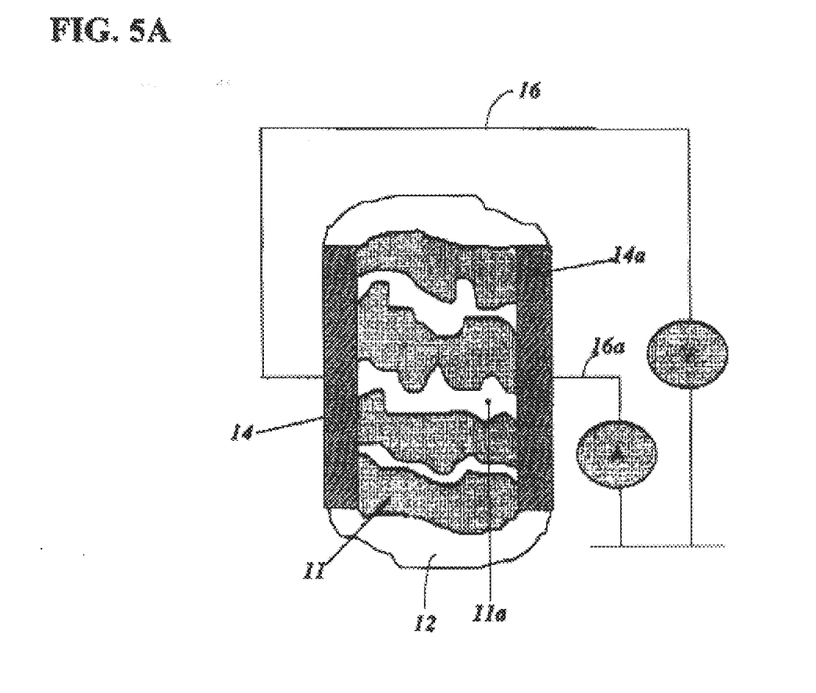
FIGS. 5A and 5B are schematic diagrams for explaining the measuring principle of the sensor shown in FIG. 4.
Figure 5B:
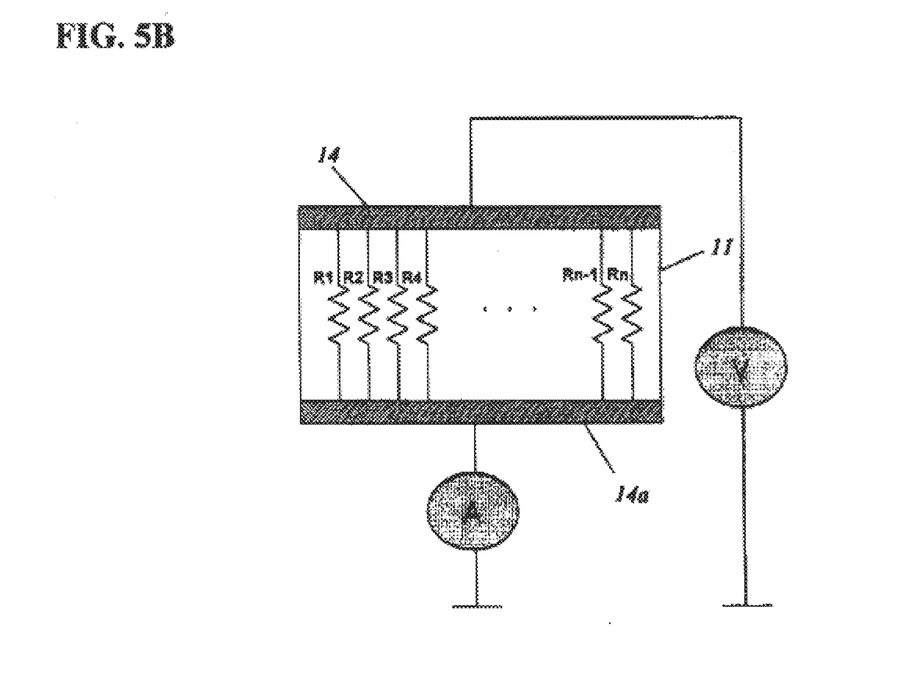

FIGS. 5A and 5B are schematic diagrams for explaining the measuring principle of the sensor shown in FIG. 4. From the drawing of FIG. 5A, it is understood that the electrodes 14 and 14a are attached to two sides of the porous ceramic 11 supported by the insulating plate 12, a plurality of pores 11a are connected between the two electrodes 14 and 14a, and the lead wires 16 and 16a are connected to the electrodes 14 and 14a. Thus, if conductive particles contained in a waste gas are absorbed into the pores 11a, the absorbed particles conduct same function of parallel resistances R1 to Rn as shown in FIG. 5B. Accordingly, if an ampere meter detects magnitude change of the current after a constant voltage is applied across two electrodes 14 and 14a, it is possible to know an amount of the absorbed particles indicative of volume and composition of a noxious gas contained in a waste gas.

Figure 6:
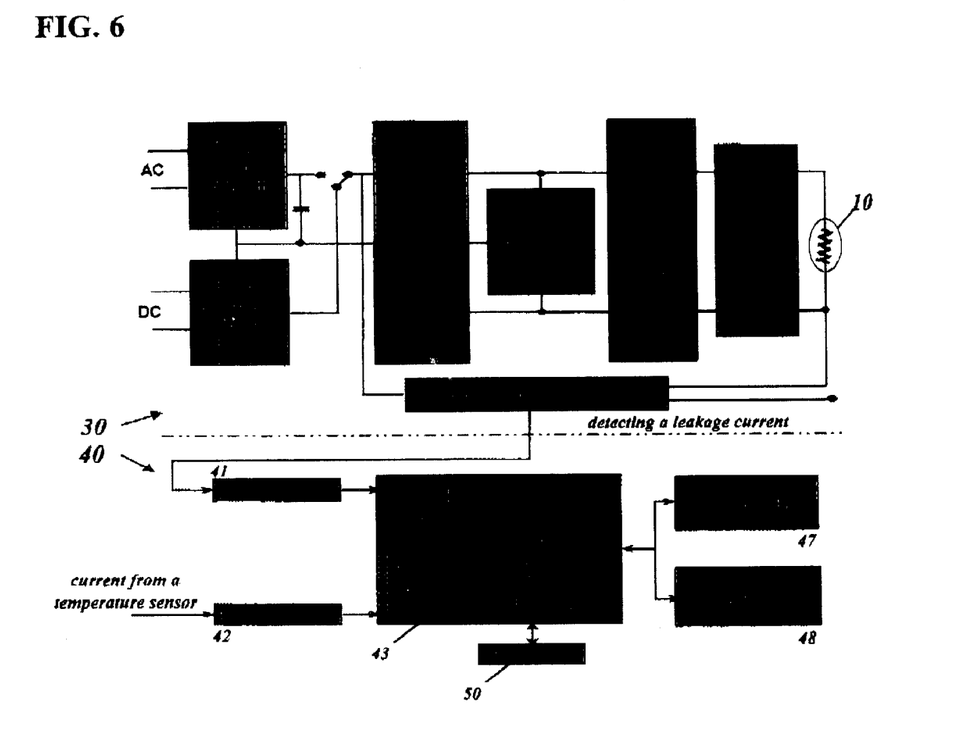
FIG. 6 is a block diagram of a waste gas measuring apparatus using the sensor configured as FIG. 4.

FIG. 6 is a block diagram of a waste gas measuring apparatus using the sensor 10 configured as FIG. 4. The apparatus of FIG. 6 comprises a measuring unit 30 applying a constant voltage to the sensor 10 and detecting a leakage current; and a main unit 40 detecting what composition a waste gas has based on the detected leakage current and a current corresponding to a present temperature which is outputted from a temperature sensor (not figured). The measuring unit 30 has a voltage source ranging from 0 to 5 kV by adopting a stepwise variable switch.

The composition detecting steps carried out by the apparatus configured as FIG. 6 are explained hereinafter.

Two amplifier 41 and 42 amplify the currents from the measuring unit 30 and the temperature sensor, respectively, and an analog/digital (A/D) converter 44, which is an internal component of a microprocessor 43, converts the amplified currents into respective digital data.

To solve problems that would be caused from common ground between the measuring unit 30 and the main unit 40 when detecting the magnitude of the leakage current, an isolating amplifier is adopted as the amplifier 41.

Figure 7:
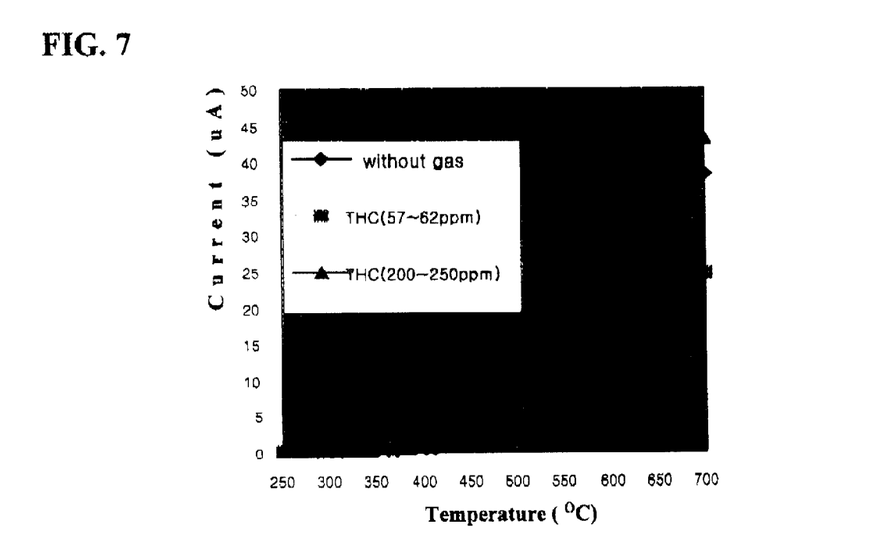
FIG. 7 shows relation curves between leakage current and temperature for each composition of a waste gas.

A CPU 45, which is executing programs pre-stored in an internal ROM, compares the converted leakage current data with a current value associated with the converted temperature data in accordance with temperature characteristic curves shown in FIG. 7, which have been stored in a memory 46. After that, the CPU 45 calculates a difference between the leakage current and temperature-associated current, determines an amount of a waste gas composition based on the difference value, and stores the determined value in the memory 46. The CPU 45 also displays the determined value through a displaying device such as a digitron or controls to turn on a LED dependently on how dense a waste gas is.

FIG. 7 shows characteristic curves of temperature vs. current of the sensor 10. From the curves shown in FIG. 7, it is clear that the leakage current detected when no gas is absorbed is different from that detected when HC, NO, or CO is absorbed, and the leakage current is dependent on the temperature.

However, the sensor 10 can provide a leakage current irrespective of an ambient temperature since it has a temperature compensating function achieved by the thermal compensating plates 15 and 15a, which means that it is possible to obtain more stable and accurate measured value for waste gas composition.

An operator or a driver can enter a command through key pad 48 to request the measured value to be transmitted to other device such as a PC 50 through a serial port 49. The PC 50 may analyze the measured values and display the analyzed result in a graphic form.

The microprocessor 43 adopted in this embodiment has internal elements of a RAM for storing data temporally; a ROM storing program permanently; and I/O port for communicating with external device, besides CPU and A/D converter. A command signal is entered to the microprocessor 43 through the key pad 48.

If a modem is installed onto or in a case of the waste gas measuring apparatus of FIG. 6 and a telephone wire is connected to the modem, a remote monitoring system for monitoring an amount of noxious waste gas can be built up. If a wireless modem is adopted, the wire connection is not necessary.

To be brief, the sensor 10 according to the present invention can measure accurately an amount of a specific gas whose conductivity is sensitive to temperature since the thermal compensating plates 15 and 15a can keep temperature constant. In addition, it is possible to store and transmit the measured data since the waste gas measuring apparatus has a general function of a computer, which enables a waste gas to be monitored remotely.

Figure 8:
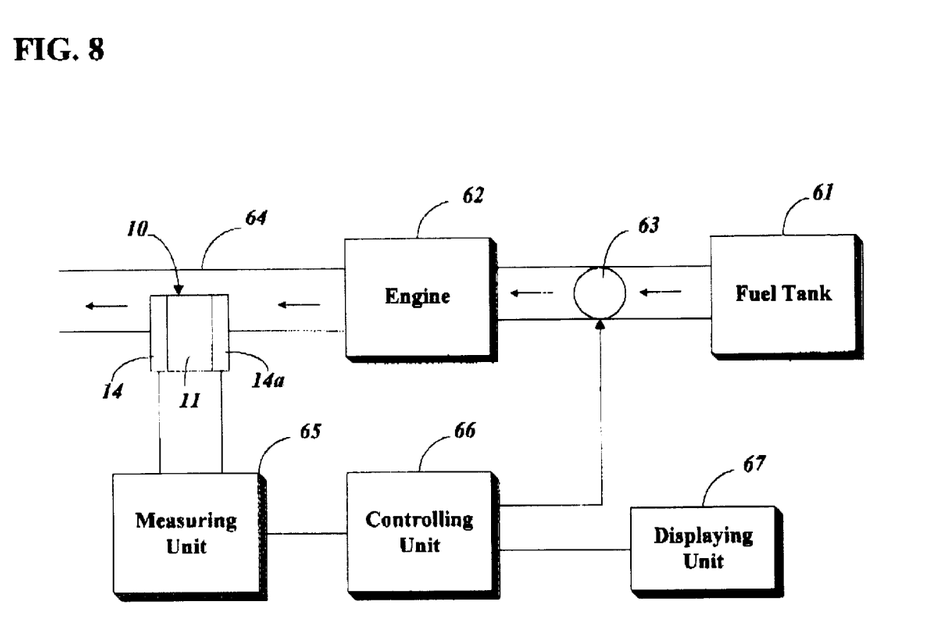
FIG. 8 is a block diagram of a fuel control apparatus equipped with the sensor configured as FIG. 4 according to the present invention.

FIG. 8 is a block diagram of a fuel control apparatus equipped with the sensor 10 according to the present invention. The apparatus of FIG. 8 comprises a fuel tank 61; a solenoid valve 63 adjusting an amount of fuel flowing into an engine 62 from the fuel tank 61; the sensor 10 outputting an electrical signal corresponding to an amount and composition of a waste gas stream exhausted through a exhaust pipe 64 due to fuel combustion; a measuring unit 65 computing an amount of gas composition based on the electrical signal from the sensor 10; a controlling unit 66 controlling the opening extent of the solenoid valve 63 based on the computed value for the amount of gas composition; a displaying unit 67 displaying the computed values numerically or turning on a LED to alarm under the control of the controlling unit 66 if one of the computed values exceeds a preset limit.

The measuring unit 65 and the controlling unit 66 may be embodied in a OBD (On Board Diagnosis) or a ECC (Electronic Concentrated engine Control) system simply, and the displaying unit 67 may be installed in a dashboard to enable a driver to know easily how much a waste gas is exhausted.

The fuel controlling steps carried out by the apparatus of FIG. 8 are explained from now on.

When an electrical signal for a leakage current is outputted from the sensor 10 installed onto the exhaust pipe 64, the measuring unit 65 computes an amount of generated noxious gas based on the leakage signal detected by the sensor 10. The controlling unit 65 keeps checking whether or not the computed value for the amount of a gas is above a pre-stored environment standard for a waste gas while controlling the displaying unit 67 to display the computed value. If the computed value exceeds an environment standard, the controlling unit 66 controls the solenoid valve to be shut a little to decrease an amount of fuel being fed into the engine 62 from the fuel tank 61 and controls the displaying unit 67 to turn on the LED to alarm a driver at the same time.

The waste gas sensor and the fuel control apparatus using the sensor according to the present invention can measure a noxious waste gas exhausted from an automobile in real time by an electrical measuring method instead of a chemical one, so that it is possible to adjust immediately an amount of fuel to burn. These abilities have the effect of making the frequency of air pollution caused by automobiles more less and reducing an amount of fuel consumption by about 10% and an amount of carbon generated from fuel combustion by about 70%.

Although the preferred embodiment of the present invention have been disclosed for illustrative purposes, those skilled in the art will appreciate that various modifications, additions and substitutions are possible, without departing from the scope and spirit of the invention as recited in the accompanying claims.

What is a claimed is:

1. A waste gas sensor, comprising:

a porous ceramic having a plurality of pores having internal surfaces formed therein, said pores adhering conductive particles to the internal surfaces thereof;

an insulating supporter supporting the porous ceramic at the bottom of the porous ceramic;

an insulating filler covering the porous ceramic;

a pair of electrodes inserted vertically into the porous ceramic through the insulating filler;

a thermal compensating plate, which is inserted vertically into the insulating filler to support the pair of electrodes, transforming electrical energy into thermal energy;

lead wires connected to each of the electrodes and the thermal compensating plate; and a insulating lid covering the top of the filler and separating the lead wires from each other, wherein the lead wires penetrate the insulating lid.

2. The sensor set forth in claim 1, wherein the electrodes are made from meshy stainless steel.

3. The sensor set forth in claim 1, further comprising a combining screw consisting of a male screw and a screw cap which are formed around the peripheral of the insulating filler.

* * * * *